US012599160B2

(12) United States Patent
Bunch et al.

(10) Patent No.: US 12,599,160 B2
(45) Date of Patent: Apr. 14, 2026

(54) LIPID-CONTAINING ORAL COMPOSITION

(71) Applicant: NICOVENTURES TRADING LIMITED, London (GB)

(72) Inventors: John E. Bunch, Cary, NC (US); Anthony Richard Gerardi, Winston-Salem, NC (US); Darrell Eugene Holton, Jr., Clemmons, NC (US); Ronald K. Hutchens, East Bend, NC (US); Thomas H. Poole, Winston-Salem, NC (US); Luis Monsalud, Kernersville, NC (US); John Paul Mua, Advance, NC (US); Frank Kelley St. Charles, Bowling Green, KY (US)

(73) Assignee: NICOVENTURES TRADING LIMITED, London (GB)

( * ) Notice: Subject to any disclaimer, the term of this patent is extended or adjusted under 35 U.S.C. 154(b) by 416 days.

(21) Appl. No.: 17/836,794

(22) Filed: Jun. 9, 2022

(65) Prior Publication Data

US 2022/0304365 A1     Sep. 29, 2022

Related U.S. Application Data

(63) Continuation of application No. PCT/IB2020/061605, filed on Dec. 7, 2020, and a continuation-in-part of application No. 16/706,974, filed on Dec. 9, 2019.

(51) Int. Cl.

| | |
|---|---|
| *A24B 15/16* | (2020.01) |
| *A24B 13/00* | (2006.01) |
| *A24B 15/30* | (2006.01) |
| *A24B 15/40* | (2006.01) |
| *A24B 15/42* | (2006.01) |
| *A61K 31/00* | (2006.01) |
| *A61K 31/465* | (2006.01) |
| *A61K 36/185* | (2006.01) |
| *A61K 47/24* | (2006.01) |
| *A61K 47/38* | (2006.01) |
| *A61K 47/44* | (2017.01) |

(52) U.S. Cl.
CPC .............. *A24B 15/16* (2013.01); *A24B 13/00* (2013.01); *A24B 15/303* (2013.01); *A24B 15/403* (2013.01); *A24B 15/42* (2013.01); *A61K 31/465* (2013.01); *A61K 31/658* (2023.05); *A61K 36/185* (2013.01); *A61K 47/24* (2013.01); *A61K 47/38* (2013.01); *A61K 47/44* (2013.01)

(58) Field of Classification Search
CPC ..... A24B 15/243; A24B 13/02; A24B 15/303; A24B 15/42
See application file for complete search history.

(56) References Cited

U.S. PATENT DOCUMENTS

| | | | |
|---|---|---|---|
| 5,417,229 | A | 5/1995 | Summers et al. |
| 6,060,078 | A | 5/2000 | Lee |
| 6,138,683 | A | 10/2000 | Hersh et al. |
| 6,845,777 | B2 | 1/2005 | Pera |
| 6,958,143 | B2 | 10/2005 | Choi et al. |
| 7,032,601 | B2 | 4/2006 | Atchley et al. |
| 7,056,541 | B1 | 6/2006 | Stahl et al. |
| 7,507,427 | B2 | 3/2009 | Andersen et al. |
| 7,810,507 | B2 | 10/2010 | Dube et al. |
| 7,833,555 | B2 | 11/2010 | Andersen et al. |
| 7,861,728 | B2 | 1/2011 | Holton, Jr. et al. |
| 7,900,637 | B2 | 3/2011 | Fagerstrom et al. |
| 7,950,399 | B2 | 5/2011 | Winterson et al. |
| 8,069,861 | B2 | 12/2011 | Sinclair |
| 8,124,147 | B2 | 2/2012 | Cheng et al. |
| 8,293,295 | B2 | 10/2012 | Andersen et al. |
| 8,336,557 | B2 | 12/2012 | Kumar et al. |
| 8,343,532 | B2 | 1/2013 | Dam et al. |
| 8,424,541 | B2 | 4/2013 | Crawford et al. |
| 8,469,036 | B2 | 6/2013 | Williams et al. |

(Continued)

FOREIGN PATENT DOCUMENTS

| | | |
|---|---|---|
| CN | 103005680 | 4/2013 |
| CN | 103263507 | 8/2013 |
| CN | 103494324 | 1/2014 |
| CN | 105192876 | 12/2015 |
| CN | 105595404 | 5/2016 |
| JP | 2018162326 A | 10/2018 |

(Continued)

OTHER PUBLICATIONS

Robichaud, Meagan et al., "Tobacco companies introduce 'tobacco free' nicotine pouches", *Tob Control 2019*, Nov. 21, 2019, 1-2, National Library of Medicine, doi:10.1136/tobaccocontrol-2019-055321.

(Continued)

*Primary Examiner* — Michael H. Wilson
*Assistant Examiner* — Jennifer A Kessie
(74) *Attorney, Agent, or Firm* — WOMBLE BOND DICKINSON (US) LLP; Scott R. Breining

(57) ABSTRACT

The disclosure provides a composition including a filler, a lipid having a melting point of about 29° C. or above, water, and a flavoring agent or an active ingredient or both a flavoring agent and an active ingredient, which is optionally substantially free of isomalt and substantially free of tobacco material, excluding any nicotine component present, based on the total weight of the composition. The disclosure also provides compositions including a filler, a lipid having a melting point of about 29° C. or above, water in an amount of at least about 15% by weight, based on total weight of the composition, and a flavoring agent or an active ingredient or both a flavoring agent and an active ingredient.

6 Claims, No Drawings

(56) References Cited

U.S. PATENT DOCUMENTS

| | | |
|---|---|---|
| 8,469,037 B2 | 6/2013 | Liu et al. |
| 8,529,875 B2 | 9/2013 | Andersen |
| 8,529,914 B2 | 9/2013 | Fuisz et al. |
| 8,545,870 B2 | 10/2013 | Dupinay et al. |
| 8,591,967 B2 | 11/2013 | Andersen et al. |
| 8,613,285 B2 | 12/2013 | Fuisz |
| 8,627,828 B2 | 1/2014 | Strickland et al. |
| 8,642,016 B2 | 2/2014 | Chau et al. |
| 8,714,163 B2 | 5/2014 | Kumar et al. |
| 8,741,348 B2 | 6/2014 | Hansson et al. |
| 8,747,562 B2 | 6/2014 | Mishra et al. |
| 8,828,361 B2 | 9/2014 | Anderson |
| 8,833,378 B2 | 9/2014 | Axelsson et al. |
| 8,846,075 B2 | 9/2014 | Johnson et al. |
| 8,858,984 B2 | 10/2014 | Dam et al. |
| 8,863,755 B2 | 10/2014 | Zhuang et al. |
| 8,871,243 B2 | 10/2014 | Fankhauser et al. |
| 8,931,493 B2 | 1/2015 | Sebastian et al. |
| 8,945,593 B2 | 2/2015 | LoCoco et al. |
| 8,978,661 B2 | 3/2015 | Atchley et al. |
| 8,992,974 B2 | 3/2015 | McCarty |
| 9,027,567 B2 | 5/2015 | Gee et al. |
| 9,039,839 B2 | 5/2015 | Beeson et al. |
| 9,044,035 B2 | 6/2015 | Jackson et al. |
| 9,084,439 B2 | 7/2015 | Holton, Jr. |
| 9,155,321 B2 | 10/2015 | Cantrell et al. |
| 9,161,567 B2 | 10/2015 | Shikata et al. |
| 9,161,908 B2 | 10/2015 | Nilsson |
| 9,167,835 B2 | 10/2015 | Sengupta et al. |
| 9,185,931 B2 | 11/2015 | Gao et al. |
| 9,204,667 B2 | 12/2015 | Cantrell et al. |
| 9,237,768 B2 | 1/2016 | Carroll et al. |
| 9,358,296 B2 | 6/2016 | McCarty |
| 9,372,033 B2 | 6/2016 | Lampe et al. |
| 9,386,800 B2 | 7/2016 | Sebastian et al. |
| 9,402,414 B2 | 8/2016 | Griscik et al. |
| 9,402,809 B2 | 8/2016 | Axelsson et al. |
| 9,414,624 B2 | 8/2016 | Carroll et al. |
| 9,420,825 B2 | 8/2016 | Beeson et al. |
| 9,468,233 B2 | 10/2016 | Macko et al. |
| 9,474,303 B2 | 10/2016 | Holton, Jr. |
| 9,521,864 B2 | 12/2016 | Gao et al. |
| 9,565,867 B2 | 2/2017 | Wittorff et al. |
| 9,629,392 B2 | 4/2017 | Holton, Jr. |
| 9,675,102 B2 | 6/2017 | Hunt et al. |
| 9,763,928 B2 | 9/2017 | Duggins et al. |
| 9,775,376 B2 | 10/2017 | Cantrell et al. |
| 9,801,409 B1 | 10/2017 | Smith |
| 9,848,634 B2 | 12/2017 | Fuisz |
| 9,854,830 B2 | 1/2018 | Gao et al. |
| 9,884,015 B2 | 2/2018 | Gao et al. |
| 9,907,748 B2 | 3/2018 | Borschke et al. |
| 9,925,145 B2 | 3/2018 | Hubinette et al. |
| 9,930,909 B2 | 4/2018 | Gao et al. |
| 9,999,243 B2 | 6/2018 | Gao et al. |
| 10,039,309 B2 | 8/2018 | Carroll et al. |
| 10,045,976 B2 | 8/2018 | Fusco et al. |
| 10,092,715 B2 | 10/2018 | Axelsson et al. |
| 10,130,120 B2 | 11/2018 | Mishra et al. |
| 10,143,230 B2 | 12/2018 | Mishra et al. |
| 10,149,850 B2 | 12/2018 | Mishra et al. |
| 10,172,810 B2 | 1/2019 | McCarty |
| 10,244,786 B2 | 4/2019 | Gao et al. |
| 10,334,873 B2 | 7/2019 | Mishra et al. |
| 10,357,054 B2 | 7/2019 | Marshall et al. |
| 10,375,984 B2 | 8/2019 | Hernandez Garcia et al. |
| 10,426,726 B2 | 10/2019 | Neergaard |
| 10,463,070 B2 | 11/2019 | Carroll et al. |
| 10,532,046 B2 | 1/2020 | Rogers et al. |
| 10,543,205 B2 | 1/2020 | Wittorff et al. |
| 2003/0003130 A1 | 1/2003 | Okubo et al. |
| 2004/0118422 A1 | 6/2004 | Lundin et al. |
| 2004/0123873 A1 | 7/2004 | Calandro et al. |
| 2007/0031539 A1 | 2/2007 | Calton, Jr. et al. |
| 2007/0122456 A1* | 5/2007 | Lindberg ............. A61K 9/0056 |
| | | 514/343 |
| 2008/0081071 A1 | 4/2008 | Sanghvi et al. |
| 2008/0166395 A1 | 7/2008 | Roush |
| 2009/0023819 A1 | 1/2009 | Axelsson |
| 2009/0041829 A1* | 2/2009 | Herslof ................ A61K 9/2077 |
| | | 424/452 |
| 2009/0065013 A1 | 3/2009 | Essen et al. |
| 2009/0142443 A1 | 6/2009 | Robinson et al. |
| 2009/0253754 A1 | 10/2009 | Selmin et al. |
| 2009/0293895 A1* | 12/2009 | Axelsson ................ A61P 25/34 |
| | | 131/352 |
| 2009/0301504 A1 | 12/2009 | Worthen et al. |
| 2010/0004294 A1 | 1/2010 | Axelsson et al. |
| 2010/0061940 A1 | 3/2010 | Axelsson et al. |
| 2010/0126520 A1 | 5/2010 | Clayton |
| 2010/0187143 A1 | 7/2010 | Essen et al. |
| 2010/0260690 A1 | 10/2010 | Kristensen et al. |
| 2010/0294292 A1 | 11/2010 | Hodin et al. |
| 2011/0139164 A1 | 6/2011 | Mua et al. |
| 2011/0220130 A1 | 9/2011 | Mua et al. |
| 2011/0268809 A1 | 11/2011 | Brinkley et al. |
| 2012/0031415 A1 | 2/2012 | Essen et al. |
| 2012/0037175 A1 | 2/2012 | Cantrell et al. |
| 2012/0107300 A1 | 5/2012 | Schirripa |
| 2012/0128734 A1 | 5/2012 | Hubinette et al. |
| 2013/0078307 A1 | 3/2013 | Holton, Jr. et al. |
| 2013/0098377 A1 | 4/2013 | Borschke |
| 2013/0118512 A1 | 5/2013 | Jackson et al. |
| 2013/0152953 A1 | 6/2013 | Mua et al. |
| 2013/0177646 A1 | 7/2013 | Hugerth et al. |
| 2013/0206150 A1 | 8/2013 | Duggins et al. |
| 2013/0209540 A1 | 8/2013 | Duggins et al. |
| 2013/0251779 A1 | 9/2013 | Svandal et al. |
| 2013/0340773 A1 | 12/2013 | Sebastian et al. |
| 2014/0130813 A1 | 5/2014 | Strehle |
| 2014/0154301 A1 | 6/2014 | Chau et al. |
| 2014/0255452 A1 | 9/2014 | Reddick et al. |
| 2015/0068544 A1 | 3/2015 | Moldoveanu et al. |
| 2015/0068545 A1 | 3/2015 | Moldoveanu et al. |
| 2015/0071972 A1 | 3/2015 | Holton, Jr. et al. |
| 2015/0096573 A1 | 4/2015 | Gao et al. |
| 2015/0096574 A1 | 4/2015 | Gao et al. |
| 2015/0096576 A1 | 4/2015 | Gao et al. |
| 2015/0101627 A1 | 4/2015 | Marshall et al. |
| 2015/0230515 A1 | 8/2015 | Lampe et al. |
| 2015/0296868 A1 | 10/2015 | Sutton |
| 2016/0000140 A1 | 1/2016 | Sebastian et al. |
| 2016/0073676 A1 | 3/2016 | Cantrell et al. |
| 2016/0073689 A1 | 3/2016 | Sebastian et al. |
| 2016/0157515 A1 | 6/2016 | Chapman et al. |
| 2016/0192703 A1 | 7/2016 | Sebastian et al. |
| 2016/0303042 A1 | 10/2016 | Yoshimura et al. |
| 2017/0007594 A1 | 1/2017 | Borschke |
| 2017/0164651 A1 | 6/2017 | Mua et al. |
| 2017/0165252 A1 | 6/2017 | Mua et al. |
| 2017/0172995 A1 | 6/2017 | Repaka et al. |
| 2017/0280764 A1 | 10/2017 | Sahlen et al. |
| 2017/0312261 A1 | 11/2017 | Changoer et al. |
| 2017/0318858 A1 | 11/2017 | Hodin et al. |
| 2018/0140007 A1 | 5/2018 | Aspgren et al. |
| 2018/0140521 A1 | 5/2018 | Geonnotti et al. |
| 2018/0140554 A1 | 5/2018 | Wittorff |
| 2018/0153211 A1 | 6/2018 | Persson |
| 2018/0235273 A1 | 8/2018 | Carroll et al. |
| 2018/0255826 A1 | 9/2018 | Persson et al. |
| 2018/0257801 A1 | 9/2018 | Persson |
| 2018/0271146 A9 | 9/2018 | Aspgren et al. |
| 2019/0000907 A1 | 1/2019 | Cohen |
| 2019/0037909 A1 | 2/2019 | Greenbaum et al. |
| 2019/0060225 A1 | 2/2019 | Mandel |
| 2019/0255035 A1 | 8/2019 | Bruun |
| 2020/0037638 A1 | 2/2020 | Faraci et al. |
| 2020/0128870 A1* | 4/2020 | Hassler .................. A24B 15/16 |
| 2020/0138706 A1 | 5/2020 | Rudraraju et al. |
| 2020/0275689 A1 | 9/2020 | Lewerenz |
| 2020/0297026 A1* | 9/2020 | Kannisto ............. A24B 15/385 |
| 2020/0305496 A1 | 10/2020 | Gessesse |
| 2020/0383372 A1* | 12/2020 | Stahl ................... A24B 15/385 |

(56) References Cited

U.S. PATENT DOCUMENTS

| | | | |
|---|---|---|---|
| 2021/0068446 A1 | 3/2021 | Keller et al. | |
| 2021/0169889 A1 | 6/2021 | Keller et al. | |
| 2021/0177738 A1 | 6/2021 | Keller et al. | |

FOREIGN PATENT DOCUMENTS

| | | | | |
|---|---|---|---|---|
| WO | 1999/015171 A1 | 4/1999 | | |
| WO | 2015/090337 A1 | 6/2015 | | |
| WO | WO 2018/197454 | 11/2018 | | |
| WO | WO-2018197454 A1 * | 11/2018 | ............. | A24B 13/00 |
| WO | WO 2019/036243 | 2/2019 | | |
| WO | WO 2019/140406 | 7/2019 | | |
| WO | WO 2020/028991 | 2/2020 | | |

OTHER PUBLICATIONS

Shit, Subhas et al., "Edible Polymers: Challenges and Opportunities", Journal of Polymers vol. 2014, Article ID 427259, 13 Pages; http://dx.doi.or/10.1155/2014/427259.
Vieira, Melissa et al., "Natural-based plasticizers and biopolymer films: A review", European Polymer Journal 47, (2011), 254-263.

* cited by examiner

LIPID-CONTAINING ORAL COMPOSITION

CROSS-REFERENCE TO RELATED APPLICATIONS

The present application is a continuation of International Application No. PCT/IB2020/061605, filed Dec. 7, 2020, and a continuation-in-part of U.S. application Ser. No. 16/706,974, filed Dec. 9, 2019, each of which are incorporated herein by reference in their entirety.

FIELD OF THE DISCLOSURE

The present disclosure relates to products intended for human use. The products are configured for oral use and deliver substances such as flavors and/or active ingredients during use. Such products may include tobacco or a component derived from tobacco, or may be tobacco-free alternatives.

BACKGROUND

Tobacco may be enjoyed in a so-called "smokeless" form. Particularly popular smokeless tobacco products are employed by inserting some form of processed tobacco or tobacco-containing formulation into the mouth of the user. Conventional formats for such smokeless tobacco products include moist snuff, snus, and chewing tobacco, which are typically formed almost entirely of particulate, granular, or shredded tobacco, and which are either portioned by the user or presented to the user in individual portions, such as in single-use pouches or sachets. Other traditional forms of smokeless products include compressed or agglomerated forms, such as plugs, tablets, or pellets. Alternative product formats, such as tobacco-containing gums and mixtures of tobacco with other plant materials, are also known. See for example, the types of smokeless tobacco formulations, ingredients, and processing methodologies set forth in U.S. Pat. No. 1,376,586 to Schwartz; U.S. Pat. No. 4,513,756 to Pittman et al.; U.S. Pat. No. 4,528,993 to Sensabaugh, Jr. et al.; U.S. Pat. No. 4,624,269 to Story et al.; U.S. Pat. No. 4,991,599 to Tibbetts; U.S. Pat. No. 4,987,907 to Townsend; U.S. Pat. No. 5,092,352 to Sprinkle, III et al.; U.S. Pat. No. 5,387,416 to White et al.; U.S. Pat. Nos. 6,668,839 and 6,834,654 to Williams; U.S. Pat. Nos. 6,953,040; 7,032,601; and 7,694,686 to Atchley et al.; U.S. Pat. Pub. No. 2004/0020503 to Williams; U.S. Pat. Pub. No. 2005/0115580 to Quinter et al.; U.S. Pat. Pub. No. 2006/0191548 to Strickland et al.; U.S. Pat. Pub. Nos. 2007/0062549; and 2007/0186941 to Holton, Jr. et al.; U.S. Pat. Pub. No. 2007/0186942 to Strickland et al.; U.S. Pat. Pub. No. 2008/0029110 to Dube et al.; U.S. Pat. Pub. Nos. 2008/0029116; and 2008/0173317 to Robinson et al.; U.S. Pat. Pub. No. 2008/0209586 to Neilsen et al.; U.S. Pat. Pub. No. 2009/0065013 to Essen et al.; and U.S. Pat. Pub. No. 2010/0282267 to Atchley, as well as WO2004/095959 to Arnarp et al., each of which is incorporated herein by reference.

Smokeless tobacco product configurations that combine tobacco material with various binders and fillers have been proposed more recently, with example product formats including lozenges, pastilles, gels, extruded forms, and the like. See, for example, the types of products described in U.S. Pat. App. Pub. No. 2008/0196730 to Engstrom et al.; U.S. Pat. App. Pub. No. 2008/0305216 to Crawford et al.; U.S. Pat. Pub. No. 2009/0293889 to Kumar et al.; U.S. Pat. Pub. No. 2010/0291245 to Gao et al; U.S. Pat. App. No. 2011/0139164 to Mua et al.; U.S. Pat. App. Pub. No.

2012/0037175 to Cantrell et al.; U.S. Pat. App. Pub. No. 2012/0055494 to Hunt et al.; U.S. Pat. App. No. 2012/0138073; and 2012/0138074 to Cantrell et al.; U.S. Pat. App. Pub. No. 2013/0074855; and 2013/0074856 to Holton, Jr.; U.S. Pat. App. Pub. No. 2013/0152953 to Mua et al.; U.S. Pat. App. Pub. No. 2013/0274296 to Jackson et al.; U.S. Pat. App. Pub. No. 2015/0068545 to Moldoveanu et al.; U.S. Pat. App. Pub. No. 2015/0101627 to Marshall et al.; and U.S. Pat. App. No. 2015/0230515 to Lampe et al., each of which is incorporated herein by reference.

BRIEF SUMMARY

The present disclosure generally provides lipid-containing compositions configured for oral use. The compositions are intended to impart a taste when used orally, and typically also deliver one or more active ingredients to the consumer, such as nicotine. The compositions are typically adapted for introduction into the oral cavity.

The disclosure includes, without limitations, the following embodiments. Where an embodiment refers to a composition as further including one or more components selected from a list, such a reference includes compositions that include a single member from a single classification of components from the list (e.g., a single sweetener), or two or more members from a single classification of components from the list (e.g., two sweeteners), or combinations of one or more members from each of two or more classifications of components from the list (e.g., a sweetener and an alkali metal salt).

The disclosure includes, without limitation, the following embodiments.

Embodiment 1: A composition, comprising: a filler, a lipid having a melting point of about 29° C. or above, water, and a flavoring agent or an active ingredient or both a flavoring agent and an active ingredient, wherein the composition is substantially free of isomalt and substantially free of tobacco material, excluding any nicotine component present.

Embodiment 2: The composition of Embodiment 1, wherein the lipid has a melting point of about 36° C. to about 45° C.

Embodiment 3: The composition of any one of Embodiments 1 to 2, wherein the lipid is selected from the group consisting of palm oil, palm kernel oil, soybean oil, cottonseed oil, and combinations thereof.

Embodiment 4: The composition of any one of Embodiments 1 to 3, further comprising a component selected from lecithin, sweeteners, salts, and mixtures thereof.

Embodiment 5: The composition of any one of Embodiments 1 to 4, comprising one or more alkali metal salts selected from the group consisting of sodium chloride, sodium carbonate, sodium bicarbonate, and combinations thereof.

Embodiment 6: The composition of any one of Embodiments 1 to 5, wherein the active ingredient is selected from the group consisting of a nicotine component, nutraceuticals, botanicals, stimulants, amino acids, vitamins, cannabinoids, cannabimimetics, terpenes, and combinations thereof.

Embodiment 7: The composition of any one of Embodiments 1 to 6, comprising from about 0.001 to about 10% by weight of a nicotine component, calculated as the free base and based on the total weight of the composition.

Embodiment 8: The composition of any one of Embodiments 1 to 7, wherein the filler is in particulate form and comprises a cellulose material.

Embodiment 9: The composition of any one of Embodiments 1 to 8, wherein the cellulose material comprises microcrystalline cellulose.

Embodiment 10: The composition of any one of Embodiments 1 to 9, wherein the filler further comprises a cellulose derivative.

Embodiment 11: The composition of any one of Embodiments 1 to 10, wherein the cellulose derivative is hydroxypropylcellulose.

Embodiment 12: A composition, comprising: a filler, a lipid having a melting point of about 29° C. or above, water in an amount of at least about 15% by weight, based on total weight of the composition, and a flavoring agent or an active ingredient or both a flavoring agent and an active ingredient.

Embodiment 13: The composition of Embodiment 12, wherein the filler is present in an amount of at least about 20% by weight, based on total dry weight of the composition.

Embodiment 14: The composition of any one of Embodiments 12 to 13, wherein the lipid is present in an amount of at least about 10% by weight, based on total dry weight of the composition. Embodiment 15: The composition of any one of Embodiments 12 to 14, wherein the water is present in an amount of at least about 20% by weight, based on total dry weight of the composition.

Embodiment 16: The composition of any one of Embodiments 12 to 15, wherein the lipid has a melting point of about 36° C. to about 45° C.

Embodiment 17: The composition of any one of Embodiments 12 to 16, further comprising a component selected from lecithin, sweeteners, salts, and mixtures thereof.

Embodiment 18: The composition of any one of Embodiments 12 to 17, wherein the active ingredient is selected from the group consisting of a nicotine component, nutraceuticals, botanicals, stimulants, amino acids, vitamins, cannabinoids, cannabimimetics, terpenes, and combinations thereof.

Embodiment 19: The composition of any one of Embodiments 12 to 18, comprising from about 0.001 to about 10% by weight of a nicotine component, calculated as the free base and based on the total weight of the composition.

Embodiment 20: The composition of any one of Embodiments 12 to 19, comprising:
about 10 to about 70% by dry weight a filler;
about 10 to about 70% by dry weight of a lipid;
about 15 to about 60% by dry weight of water;
about 0.1 to about 5% by dry weight of one or more alkali metal salts; and
about 0.001 to about 10% by dry weight of an active ingredient selected from the group consisting of a nicotine component, nutraceuticals, botanicals, stimulants, amino acids, vitamins, cannabinoids, cannabimimetics, terpenes, and combinations thereof.

These and other features, aspects, and advantages of the disclosure will be apparent from a reading of the following detailed description. The invention includes any combination of two, three, four, or more of the above-noted embodiments as well as combinations of any two, three, four, or more features or elements set forth in this disclosure, regardless of whether such features or elements are expressly combined in a specific embodiment description herein. This disclosure is intended to be read holistically such that any separable features or elements of the disclosed invention, in any of its various aspects and embodiments, should be viewed as intended to be combinable unless the context clearly dictates otherwise.

DETAILED DESCRIPTION

The present disclosure will now be described more fully hereinafter with reference to example embodiments thereof. These example embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in this specification and the claims, the singular forms "a," "an," and "the" include plural referents unless the context clearly dictates otherwise. Reference to "dry weight percent" or "dry weight basis" refers to weight on the basis of dry ingredients (i.e., all ingredients except water). Reference to "wet weight" refers to the weight of the composition including water. Unless otherwise indicated, reference to "weight percent" of a composition reflects the total wet weight of the composition (i.e., including water).

The present disclosure relates to oral compositions, which are typically adapted for oral use, and which utilize a lipid in combination with a filler, water, and a flavoring agent or an active ingredient or both a flavoring agent and an active ingredient. Although not bound by a theory of operation, the use of a lipid in such compositions is believed to provide advantageous binding properties, and in certain embodiments, can also enhance release characteristics of flavorants or other components of the composition into the oral cavity, which can improve organoleptic properties of the composition. The example individual components of the composition are described herein below.

Lipid

The lipid of the composition is typically a fat, an oil including fractionated oils, or a wax substance derived from animal or plant material (e.g., plant-derived fats), and typically comprises mostly triglycerides along with lesser amounts of free fatty acids and mono- or di-glycerides. In certain embodiments, the lipid is a solid or semi-solid at room temperature (i.e., 25° C.) and capable of at least partially liquefying when subjected to the temperature of the oral cavity of the user. Example plant-derived fats are comprised primarily of saturated or unsaturated fatty acid chains (most of which are bound within triglyceride structures) having a carbon length of about 10 to about 26 carbon atoms, or about 14 to about 20 carbon atoms, or about 14 to about 18 carbon atoms. In certain embodiments, the plant-derived fats of the present disclosure include palm oil, palm kernel oil, soybean oil, cottonseed oil, and mixtures thereof. The lipid can be, for example, hydrogenated, partially hydrogenated, or non-hydrogenated. In one embodiment, the lipid is a blend of palm oil and palm kernel oil. Example embodiments of lipids can be purchased under the brand names CEBES®, CISAO®, or CONFAO®, available from AarhusKarlshamn USA Inc.

The melting point of the lipid is typically about 29° C. or above, such as about 29° C. to about 49° C., or about 36° C. to about 45° C., or about 38° C. to about 41° C. In some embodiments, use of lipids with a melting point of less than about 36° C. is not advantageous due to possible melting during product storage or handling. One test for determining the melting point of lipids is the Mettler dropping point method (ASTM D3954-15, Standard Test Method for Dropping Point of Waxes, ASTM International, West Conshohocken, PA, 2015, www.astm.org.).

The amount of lipid within the composition may vary. In certain embodiments, the amount of lipid is at least about 10 percent, at least about 20 percent, or at least about 30 percent, on a dry weight basis of the composition. In certain embodiments, the amount of lipid is less than about 70 percent, less than about 60 percent, or less than about 50 weight percent, on a dry weight basis. Example lipid weight ranges include about 10 to about 70 dry weight percent, such as about 20 to about 50 dry weight percent.

In certain embodiments, lecithin can be added to the composition to provide smoother textural properties of the composition and to improve flowability and mixing of the lipid with the remaining components of the composition. Lecithin can be used in an amount of about 0.01 to about 5% by dry weight of the composition, such as about 0.1 to about 2.5% or about 0.1 to about 1.0%.

Filler

Certain embodiments of the compositions described herein may also include at least one filler. Such fillers may fulfill multiple functions, such as enhancing certain organoleptic properties like texture and mouthfeel. Generally, the fillers are particulate materials and are cellulose-based. In certain embodiments, the filler is also a porous material. For example, suitable particulate fillers are any non-tobacco plant material or derivative thereof, including cellulose materials derived from such sources. Examples of cellulosic non-tobacco plant material include cereal grains (e.g., maize, oat, barley, rye, buckwheat, and the like), sugar beet (e.g., FIBREX® brand filler available from International Fiber Corporation), bran fiber, and mixtures thereof. Non-limiting examples of derivatives of non-tobacco plant material include starches (e.g., from potato, wheat, rice, corn), natural cellulose, and modified cellulosic materials. Additional examples of potential particulate fillers include maltodextrin, dextrose, calcium carbonate, calcium phosphate, lactose, mannitol, xylitol, and sorbitol. Combinations of fillers can also be used.

"Starch" as used herein may refer to pure starch from any source, modified starch, or starch derivatives. Starch is present, typically in granular form, in almost all green plants and in various types of plant tissues and organs (e.g., seeds, leaves, rhizomes, roots, tubers, shoots, fruits, grains, and stems). Starch can vary in composition, as well as in granular shape and size. Often, starch from different sources has different chemical and physical characteristics. A specific starch can be selected for inclusion in the composition based on the ability of the starch material to impart a specific organoleptic property to composition. Starches derived from various sources can be used. For example, major sources of starch include cereal grains (e.g., rice, wheat, and maize) and root vegetables (e.g., potatoes and cassava). Other examples of sources of starch include acorns, arrowroot, arracacha, bananas, barley, beans (e.g., favas, lentils, mung beans, peas, chickpeas), breadfruit, buckwheat, canna, chestnuts, colacasia, katakuri, kudzu, malanga, millet, oats, oca, Polynesian arrowroot, sago, sorghum, sweet potato, quinoa, rye, tapioca, taro, tobacco, water chestnuts, and yams. Certain starches are modified starches. A modified starch has undergone one or more structural modifications, often designed to alter its high heat properties. Some starches have been developed by genetic modifications, and are considered to be "genetically modified" starches. Other starches are obtained and subsequently physically (e.g., heat, cool water swelling, etc.), chemically, or enzymatically modified. For example, modified starches can be starches that have been subjected to chemical reactions, such as esterification, etherification, oxidation, depolymerization (thinning) by acid catalysis or oxidation in the presence of base, bleaching, transglycosylation and depolymerization (e.g., dextrinization in the presence of a catalyst), cross-linking, acetylation, hydroxypropylation, and/or partial hydrolysis. Enzymatic treatment includes subjecting native starches to enzyme isolates or concentrates, microbial enzymes, and/or enzymes native to plant materials, e.g., amylase present in corn kernels to modify corn starch. Other starches are modified by heat treatments, such as pregelatinization, dextrinization, and/or cold water swelling processes. Certain modified starches include monostarch phosphate, distarch glycerol, distarch phosphate esterified with sodium trimetaphosphate, phosphate distarch phosphate, acetylated distarch phosphate, starch acetate esterified with acetic anhydride, starch acetate esterified with vinyl acetate, acetylated distarch adipate, acetylated distarch glycerol, hydroxypropyl starch, hydroxypropyl distarch glycerol, starch sodium octenyl succinate.

In some embodiments, the particulate filler is a cellulose material or cellulose derivative. One particularly suitable particulate filler for use in the products described herein is microcrystalline cellulose ("MCC"). The MCC may be synthetic or semi-synthetic, or it may be obtained entirely from natural celluloses. The MCC may be selected from the group consisting of AVICEL® grades PH-100, PH-102, PH-103, PH-105, PH-112, PH-113, PH-200, PH-300, PH-302, VIVACEL® grades 101, 102, 12, 20 and EMOCEL® grades 50M and 90M, and the like, and mixtures thereof. In one embodiment, the composition comprises MCC as the particulate filler component. The quantity of MCC present in the composition as described herein may vary according to the desired properties.

The amount of filler can vary, but is typically up to about 70 percent of the composition by weight, based on the total dry weight of the composition. A typical range of particulate filler (e.g., MCC) within the composition can be from about 0.1 to about 70 percent by total dry weight of the composition, for example, from about 1.0, about 1.5, about 2.0, about 2.5, or about 3.0, to about 20, about 30, about 40, or about 50 weight percent. An example range of filler content is about 5 to about 60 dry weight percent, such as about 10 to about 60% or about 20 to about 50%.

In one embodiment, the particulate filler further comprises a cellulose derivative or a combination of such derivatives. In some embodiments, the composition comprises from about 0.1 to about 10% of the cellulose derivative by dry weight, with certain embodiments comprising about 0.1 to about 5% by weight of cellulose derivative. In certain embodiments, the cellulose derivative is a cellulose ether (including carboxyalkyl ethers), meaning a cellulose polymer with the hydrogen of one or more hydroxyl groups in the cellulose structure replaced with an alkyl, hydroxyalkyl, or aryl group. Non-limiting examples of such cellulose derivatives include methylcellulose, hydroxypropylcellulose ("HPC"), hydroxypropylmethylcellulose ("HPMC"), hydroxyethyl cellulose, and carboxymethylcellulose ("CMC"). In one embodiment, the cellulose derivative is one or more of methylcellulose, HPC, HPMC, hydroxyethyl cellulose, and CMC. In one embodiment, the cellulose derivative is HPC. In some embodiments, the composition comprises from about 1 to about 3% HPC by dry weight.

Water

The water content of the composition, prior to use by a consumer of the product, may vary according to the desired properties. In certain embodiments, the water content is relatively low, such as less than about 10% or less than about 7.5%, or less than about 5% by total weight of the composition. In other embodiments, water is present in higher amounts, which can be particularly advantageous when combined with the lipid. Such compositions provide attributes of both aqueous-based compositions and oil-based compositions, which can combine the desirable organoleptic properties from both types of compositions. For example, compositions of the invention can include about 15 to about 60% by weight water (e.g., about 20 to about 50% or about 25 to about 40%).

Flavoring Agent

As used herein, a "flavoring agent" or "flavorant" is any flavorful or aromatic substance capable of altering the sensory characteristics associated with the oral product. Examples of sensory characteristics that can be modified by the flavoring agent include taste, mouthfeel, moistness, coolness/heat, and/or fragrance/aroma. Flavoring agents may be natural or synthetic, and the character of the flavors imparted thereby may be described, without limitation, as fresh, sweet, herbal, confectionary, floral, fruity, or spicy. Specific types of flavors include, but are not limited to, vanilla, coffee, chocolate/cocoa, cream, mint, spearmint, menthol, peppermint, wintergreen, eucalyptus, lavender, cardamon, nutmeg, cinnamon, clove, cascarilla, sandalwood, honey, jasmine, ginger, anise, sage, licorice, lemon, orange, apple, peach, lime, cherry, strawberry, and any combinations thereof. See also, Leffingwell et al., Tobacco Flavoring for Smoking Products, R. J. Reynolds Tobacco Company (1972), which is incorporated herein by reference. Flavorings also may include components that are considered moistening, cooling or smoothening agents, such as eucalyptus. These flavors may be provided neat (i.e., alone) or in a composite, and may be employed as concentrates or flavor packages (e.g., spearmint and menthol, orange and cinnamon; lime, pineapple, and the like). Representative types of components also are set forth in U.S. Pat. No. 5,387,416 to White et al.; U.S. patent application Pub. No. 2005/0244521 to Strickland et al.; and PCT Application Pub. No. WO 05/041699 to Quinter et al., each of which is incorporated herein by reference. In some instances, the flavoring agent may be provided in a spray-dried form or a liquid form.

The flavoring agent generally comprises at least one volatile flavor component. As used herein, "volatile" refers to a chemical substance that forms a vapor readily at ambient temperatures (i.e., a chemical substance that has a high vapor pressure at a given temperature relative to a nonvolatile substance). Typically, a volatile flavor component has a molecular weight below about 400 Da, and often include at least one carbon-carbon double bond, carbon-oxygen double bond, or both. In one embodiment, the at least one volatile flavor component comprises one or more alcohols, aldehydes, aromatic hydrocarbons, ketones, esters, terpenes, terpenoids, or a combination thereof. Non-limiting examples of aldehydes include vanillin, ethyl vanillin, p-anisaldehyde, hexanal, furfural, isovaleraldehyde, cuminaldehyde, benzaldehyde, and citronellal. Non-limiting examples of ketones include 1-hydroxy-2-propanone and 2-hydroxy-3-methyl-2-cyclopentenone-1-one. Non-limiting examples of esters include allyl hexanoate, ethyl heptanoate, ethyl hexanoate, isoamyl acetate, and 3-methylbutyl acetate. Non-limiting examples of terpenes include sabinene, limonene, gamma-terpinene, beta-farnesene, nerolidol, thujone, myrcene, geraniol, nerol, citronellol, linalool, and eucalyptol. In one embodiment, the at least one volatile flavor component comprises one or more of ethyl vanillin, cinnamaldehyde, sabinene, limonene, gamma-terpinene, beta-farnesene, or citral. In one embodiment, the at least one volatile flavor component comprises ethyl vanillin.

The amount of flavoring agent utilized in the composition can vary, but is typically up to about 10 weight percent, and certain embodiments are characterized by a flavoring agent content of at least about 0.1 weight percent, such as about 0.5 to about 10 weight percent, about 1 to about 6 weight percent, or about 2 to about 5 weight percent, based on the total dry weight of the composition.

Active Ingredient

The composition as disclosed herein includes one or more active ingredients. As used herein, an "active ingredient" refers to one or more substances belonging to any of the following categories: API (active pharmaceutical ingredient), food additives, natural medicaments, and naturally occurring substances that can have an effect on humans. Example active ingredients include any ingredient known to impact one or more biological functions within the body, such as ingredients that furnish pharmacological activity or other direct effect in the diagnosis, cure, mitigation, treatment, or prevention of disease, or which affect the structure or any function of the body of humans (e.g., provide a stimulating action on the central nervous system, have an energizing effect, an antipyretic or analgesic action, or an otherwise useful effect on the body). In some embodiments, the active ingredient may be of the type generally referred to as dietary supplements, nutraceuticals, "phytochemicals" or "functional foods." These types of additives are sometimes defined in the art as encompassing substances typically available from naturally-occurring sources (e.g., botanical materials) that provide one or more advantageous biological effects (e.g., health promotion, disease prevention, or other medicinal properties), but are not classified or regulated as drugs.

Non-limiting examples of active ingredients include those falling in the categories of botanical ingredients, stimulants, amino acids, nicotine components, and/or pharmaceutical, nutraceutical, and medicinal ingredients (e.g., vitamins, such as A, B3, B6, B12, and C, and/or cannabinoids, such as tetrahydrocannabinol (THC) and cannabidiol (CBD)). Each of these categories is further described herein below. The particular choice of active ingredients will vary depending upon the desired flavor, texture, and desired characteristics of the particular product.

In certain embodiments, the active ingredient is selected from the group consisting of caffeine, taurine, GABA, theanine, vitamin C, lemon balm extract, ginseng, citicoline, sunflower lecithin, and combinations thereof. For example, the active ingredient can include a combination of caffeine, theanine, and optionally ginseng. In another embodiment, the active ingredient includes a combination of theanine, gamma-amino butyric acid (GABA), and lemon balm extract. In a further embodiment, the active ingredient includes theanine, theanine and tryptophan, or theanine and one or more B vitamins (e.g., vitamin B6 or B12). In a still further embodiment, the active ingredient includes a combination of caffeine, taurine, and vitamin C.

The particular percentages of active ingredients present will vary depending upon the desired characteristics of the particular product. Typically, an active ingredient or combination thereof is present in a total concentration of at least about 0.001% by weight of the composition, such as in a range from about 0.001% to about 20%. In some embodiments, the active ingredient or combination of active ingredients is present in a concentration from about 0.1% w/w to about 10% by weight, such as, e.g., from about 0.5% w/w to about 10%, from about 1% to about 10%, from about 1% to about 5% by weight, based on the total weight of the composition. In some embodiments, the active ingredient or combination of active ingredients is present in a concentration of from about 0.001%, about 0.01%, about 0.1%, or about 1%, up to about 20% by weight, such as, e.g., from about 0.001%, about 0.002%, about 0.003%, about 0.004%, about 0.005%, about 0.006%, about 0.007%, about 0.008%, about 0.009%, about 0.01%, about 0.02%, about 0.03%, about 0.04%, about 0.05%, about 0.06%, about 0.07%, about 0.08%, about 0.09%, about 0.1%, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, or about 20% by weight, based on the total weight of the composition.

Further suitable ranges for specific active ingredients are provided herein below.

Botanical

In some embodiments, the active ingredient comprises a botanical ingredient. As used herein, the term "botanical ingredient" or "botanical" refers to any plant material or fungal-derived material, including plant material in its natural form and plant material derived from natural plant materials, such as extracts or isolates from plant materials or treated plant materials (e.g., plant materials subjected to heat treatment, fermentation, bleaching, or other treatment processes capable of altering the physical and/or chemical nature of the material). For the purposes of the present disclosure, a "botanical" includes, but is not limited to, "herbal materials," which refer to seed-producing plants that do not develop persistent woody tissue and are often valued for their medicinal or sensory characteristics (e.g., teas or tisanes). Reference to botanical material as "non-tobacco" is intended to exclude tobacco materials (i.e., does not include any *Nicotiana* species). In some embodiments, the compositions as disclosed herein can be characterized as free of any tobacco material (e.g., any embodiment as disclosed herein may be completely or substantially free of any tobacco material). By "substantially free" is meant that no tobacco material has been intentionally added. For example, certain embodiments can be characterized as having less than 0.001% by weight of tobacco, or less than 0.0001%, or even 0% by weight of tobacco.

When present, a botanical is typically at a concentration of from about 0.01% w/w to about 10% by weight, such as, e.g., from about 0.01% w/w, about 0.05%, about 0.1%, or about 0.5%, to about 1%, about 2%, about 3%, about 4%, about 5%, about 6%, about 7%, about 8%, about 9%, or about 10%, about 11%, about 12%, about 13%, about 14%, or about 15% by weight, based on the total weight of the composition.

The botanical materials useful in the present disclosure may comprise, without limitation, any of the compounds and sources set forth herein, including mixtures thereof. Certain botanical materials of this type are sometimes referred to as dietary supplements, nutraceuticals, "phytochemicals" or "functional foods." Certain botanicals, as the plant material or an extract thereof, have found use in traditional herbal medicine, and are described further herein. Non-limiting examples of botanicals or botanical-derived materials include ashwagandha, Bacopa monniera, baobab, basil, *Centella asiatica*, Chai-hu, chamomile, cherry blossom, chlorophyll, cinnamon, citrus, cloves, cocoa, cordyceps, curcumin, damiana, *Dorstenia arifolia, Dorstenia odorata*, essential oils, eucalyptus, fennel, *Galphimia glauca*, ginger, *Ginkgo biloba*, ginseng (e.g., *Panax ginseng*), green tea, *Griffonia simplicifolia*, guarana, cannabis, hemp, hops, jasmine, *Kaempferia parviflora* (Thai ginseng), kava, lavender, lemon balm, lemongrass, licorice, lutein, maca, matcha, Nardostachys chinensis, oil-based extract of *Viola odorata*, peppermint, quercetin, resveratrol, *Rhizoma gastrodiae, Rhodiola, rooibos*, rose essential oil, rosemary, *Sceletium tortuosum*, Schisandra, Skullcap, spearmint extract, Spikenard, terpenes, tisanes, turmeric, *Turnera aphrodisiaca*, valerian, white mulberry, and *Yerba mate*.

In some embodiments, the active ingredient comprises lemon balm. Lemon balm (*Melissa officinals*) is a mildly lemon-scented herb from the same family as mint (*Lamiaceae*). The herb is native to Europe, North Africa, and West Asia. The tea of lemon balm, as well as the essential oil and the extract, are used in traditional and alternative medicine. In some embodiments, the active ingredient comprises lemon balm extract. In some embodiments, the lemon balm extract is present in an amount of from about 1 to about 4% by weight, based on the total weight of the composition.

In some embodiments, the active ingredient comprises ginseng. Ginseng is the root of plants of the genus *Panax*, which are characterized by the presence of unique steroid saponin phytochemicals (ginsenosides) and gintonin. Ginseng finds use as a dietary supplement in energy drinks or herbal teas, and in traditional medicine. Cultivated species include Korean ginseng (*P. ginseng*), South China ginseng (*P. notoginseng*), and American ginseng (*P. quinquefolius*). American ginseng and Korean ginseng vary in the type and quantity of various ginsenosides present. In some embodiments, the ginseng is American ginseng or Korean ginseng. In specific embodiments, the active ingredient comprises Korean ginseng. In some embodiments, ginseng is present in an amount of from about 0.4 to about 0.6% by weight, based on the total weight of the composition.

Stimulants

In some embodiments, the active ingredient comprises one or more stimulants. As used herein, the term "stimulant" refers to a material that increases activity of the central nervous system and/or the body, for example, enhancing focus, cognition, vigor, mood, alertness, and the like. Non-limiting examples of stimulants include caffeine, theacrine, theobromine, and theophylline. Theacrine (1,3,7,9-tetramethyluric acid) is a purine alkaloid which is structurally related to caffeine, and possesses stimulant, analgesic, and anti-inflammatory effects. Present stimulants may be natural, naturally derived, or wholly synthetic. For example, certain botanical materials (guarana, tea, coffee, cocoa, and the like) may possess a stimulant effect by virtue of the presence of e.g., caffeine or related alkaloids, and accordingly are "natural" stimulants. By "naturally derived" is meant the stimulant (e.g., caffeine, theacrine) is in a purified form, outside its natural (e.g., botanical) matrix. For example, caffeine can be obtained by extraction and purification from botanical sources (e.g., tea). By "wholly synthetic", it is meant that the stimulant has been obtained by chemical synthesis. In some embodiments, the active ingredient comprises caffeine. In some embodiments, the caffeine is present in an encapsulated form. On example of an encapsulated caffeine is Vitashure®, available from Balchem Corp., 52 Sunrise Park Road, New Hampton, NY, 10958.

When present, a stimulant or combination of stimulants (e.g., caffeine, theacrine, and combinations thereof) is typically at a concentration of from about 0.1% w/w to about 15% by weight, such as, e.g., from about 0.1% w/w, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, about 10%, about 11%, about 12%, about 13%, about 14%, or about 15% by weight, based on the total weight of the composition. In some embodiments, the composition comprises caffeine in an amount of from about 1.5 to about 6% by weight, based on the total weight of the composition;

Amino Acids

In some embodiments, the active ingredient comprises an amino acid. As used herein, the term "amino acid" refers to an organic compound that contains amine ($-NH_2$) and carboxyl ($-COOH$) or sulfonic acid ($SO_3H$) functional groups, along with a side chain (R group), which is specific to each amino acid. Amino acids may be proteinogenic or non-proteinogenic. By "proteinogenic" is meant that the amino acid is one of the twenty naturally occurring amino acids found in proteins. The proteinogenic amino acids include alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. By "non-proteinogenic" is meant that either the amino acid is not found naturally in protein, or is not directly produced by cellular machinery (e.g., is the product of post-tranlational modification). Non-limiting examples of non-proteinogenic amino acids include gamma-aminobutyric acid (GABA), taurine (2-aminoethanesulfonic acid), theanine (L-γ-giutarnylethylamide), hydroxyproline, and beta-alanine. In some embodiments, the active ingredient comprises theanine. In some embodiments, the active ingredient comprises GABA. In some embodiments, the active ingredient comprises a combination of theanine and GABA. In some embodiments, the active ingredient is a combination of theanine, GABA, and lemon balm. In some embodiments, the active ingredient is a combination of caffeine, theanine, and ginseng. In some embodiments, the active ingredient comprises taurine. In some embodiments, the active ingredient is a combination of caffeine and taurine.

When present, an amino acid or combination of amino acids (e.g., theanine, GABA, and combinations thereof) is typically at a concentration of from about 0.1% w/w to about 15% by weight, such as, e.g., from about 0.1% w/w, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, about 10%, about 11%, about 12%, about 13%, about 14%, or about 15% by weight, based on the total weight of the composition.

Vitamins

In some embodiments, the active ingredient comprises a vitamin or combination of vitamins. As used herein, the term "vitamin" refers to an organic molecule (or related set of molecules) that is an essential micronutrient needed for the proper functioning of metabolism in a mammal. There are thirteen vitamins required by human metabolism, which are: vitamin A (as all-trans-retinol, all-trans-retinyl-esters, as well as all-trans-beta-carotene and other provitamin A carotenoids), vitamin B1 (thiamine), vitamin B2 (riboflavin), vitamin B3 (niacin), vitamin B5 (pantothenic acid), vitamin B6 (pyridoxine), vitamin B7 (biotin), vitamin B9 (folic acid or folate), vitamin B12 (cobalamins), vitamin C (ascorbic acid), vitamin D (calciferols), vitamin E (tocopherols and tocotrienols), and vitamin K (quinones). In some embodiments, the active ingredient comprises vitamin C. In some embodiments, the active ingredient is a combination of vitamin C, caffeine, and taurine.

When present, a vitamin or combination of vitamins (e.g., vitamin B6, vitamin B12, vitamin E, vitamin C, or a combination thereof) is typically at a concentration of from about 0.01% w/w to about 6% by weight, such as, e.g., from about 0.01%, about 0.02%, about 0.03%, about 0.04%, about 0.05%, about 0.06%, about 0.07%, about 0.08%, about 0.09%, or about 0.1% w/w, to about 0.2%, about 0.3%, about 0.4%, about 0.5% about 0.6%, about 0.7%, about 0.8%, about 0.9%, about 1%, about 2%, about 3%, about 4%, about 5%, or about 6% by weight, based on the total weight of the composition.

Antioxidants

In some embodiments, the active ingredient comprises one or more antioxidants. As used herein, the term "antioxidant" refers to a substance which prevents or suppresses oxidation by terminating free radical reactions, and may delay or prevent some types of cellular damage. Antioxidants may be naturally occurring or synthetic. Naturally occurring antioxidants include those found in foods and botanical materials. Non-limiting examples of antioxidants include certain botanical materials, vitamins, polyphenols, and phenol derivatives.

Examples of botanical materials which are associated with antioxidant characteristics include without limitation acai berry, alfalfa, allspice, annatto seed, apricot oil, basil, bee balm, wild bergamot, black pepper, blueberries, borage seed oil, bugleweed, cacao, calamus root, catnip, catuaba, cayenne pepper, chaga mushroom, chervil, cinnamon, dark chocolate, potato peel, grape seed, ginseng, gingko biloba, Saint John's Wort, saw palmetto, green tea, black tea, black cohosh, cayenne, chamomile, cloves, cocoa powder, cranberry, dandelion, grapefruit, honeybush, echinacea, garlic, evening primrose, feverfew, ginger, goldenseal, hawthorn, hibiscus flower, jiaogulan, kava, lavender, licorice, marjoram, milk thistle, mints (menthe), oolong tea, beet root, orange, oregano, papaya, pennyroyal, peppermint, red clover, rooibos (red or green), rosehip, rosemary, sage, clary sage, savory, spearmint, spirulina, slippery elm bark, sorghum bran hi-tannin, sorghum grain hi-tannin, sumac bran, comfrey leaf and root, goji berries, gutu kola, thyme, turmeric, uva ursi, valerian, wild yam root, wintergreen, yacon root, yellow dock, yerba mate, yerba santa, bacopa monniera, withania somnifera, Lion's mane, and silybum marianum. Such botanical materials may be provided in fresh or dry form, essential oils, or may be in the form of an extracts. The botanical materials (as well as their extracts) often include compounds from various classes known to provide antioxidant effects, such as minerals, vitamins, isoflavones, phytoesterols, allyl sulfides, dithiolthiones, isothiocyanates, indoles, lignans, flavonoids, polyphenols, and carotenoids. Examples of compounds found in botanical extracts or oils include ascorbic acid, peanut endocarb, resveratrol, sulforaphane, beta-carotene, lycopene, lutein, co-enzyme Q, carnitine, quercetin, kaempferol, and the like. See, e.g., Santhosh et al., Phytomedicine, 12(2005) 216-220, which is incorporated herein by reference.

Non-limiting examples of other suitable antioxidants include citric acid, Vitamin E or a derivative thereof, a tocopherol, epicatechol, epigallocatechol, epigallocatechol gallate, erythorbic acid, sodium erythorbate, 4-hexylresorcinol, theaflavin, theaflavin monogallate A or B, theaflavin digallate, phenolic acids, glycosides, quercitrin, isoquercitrin, hyperoside, polyphenols, catechols, resveratrols, oleuropein, butylated hydroxyanisole (BHA), butylated hydroxytoluene (BHT), tertiary butylhydroquinone (TBHQ), and combinations thereof.

When present, an antioxidant is typically at a concentration of from about 0.001% w/w to about 10% by weight, such as, e.g., from about 0.001%, about 0.005%, about 0.01% w/w, about 0.05%, about 0.1%, or about 0.5%, to about 1%, about 2%, about 3%, about 4%, about 5%, about 6%, about 7%, about 8%, about 9%, or about 10%, based on the total weight of the composition.

Nicotine Component

In certain embodiments, a nicotine component may be included in the composition. By "nicotine component" is meant any suitable form of nicotine (e.g., free base or salt) for providing oral absorption of at least a portion of the nicotine present. Typically, the nicotine component is selected from the group consisting of nicotine free base and a nicotine salt. In some embodiments, nicotine is in its free base form, which easily can be adsorbed in for example, a microcrystalline cellulose material to form a microcrystalline cellulose-nicotine carrier complex. See, for example, the discussion of nicotine in free base form in U.S. Pat. Pub. No. 2004/0191322 to Hansson, which is incorporated herein by reference.

In some embodiments, at least a portion of the nicotine can be employed in the form of a salt. Salts of nicotine can be provided using the types of ingredients and techniques set forth in U.S. Pat. No. 2,033,909 to Cox et al. and Perfetti, *Beitrage Tabakforschung Int.*, 12: 43-54 (1983), which are incorporated herein by reference. Additionally, salts of nicotine are available from sources such as Pfaltz and Bauer, Inc. and K&K Laboratories, Division of ICN Biochemicals, Inc. Typically, the nicotine component is selected from the group consisting of nicotine free base, a nicotine salt such as hydrochloride, dihydrochloride, monotartrate, bitartrate, sulfate, salicylate, and nicotine zinc chloride. In some embodiments, the nicotine component or a portion thereof is a nicotine salt with at least a portion of the one or more organic acids as disclosed herein above.

In some embodiments, at least a portion of the nicotine can be in the form of a resin complex of nicotine, where nicotine is bound in an ion-exchange resin, such as nicotine polacrilex, which is nicotine bound to, for example, a polymethacrilic acid, such as Amberlite IRP64, Purolite C115HMR, or Doshion P551. See, for example, U.S. Pat. No. 3,901,248 to Lichtneckert et al., which is incorporated herein by reference. Another example is a nicotine-polyacrylic carbomer complex, such as with Carbopol 974P. In some embodiments, nicotine may be present in the form of a nicotine polyacrylic complex.

Typically, the nicotine component (calculated as the free base) when present, is in a concentration of at least about 0.001% by weight of the composition, such as in a range from about 0.001% to about 10%. In some embodiments, the nicotine component is present in a concentration from about 0.1% w/w to about 10% by weight, such as, e.g., from about 0.1% w/w, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, or about 10% by weight, calculated as the free base and based on the total weight of the composition. In some embodiments, the nicotine component is present in a concentration from about 0.1% w/w to about 3% by weight, such as, e.g., from about 0.1% w/w to about 2.5%, from about 0.1% to about 2.0%, from about 0.1% to about 1.5%, or from about 0.1% to about 1% by weight, calculated as the free base and based on the total weight of the composition. These ranges can also apply to other active ingredients noted herein.

In some embodiments, the products or compositions of the disclosure can be characterized as free of any nicotine component (e.g., any embodiment as disclosed herein may be completely or substantially free of any nicotine component). By "substantially free" is meant that no nicotine has been intentionally added, beyond trace amounts that may be naturally present in e.g., a botanical material. For example, certain embodiments can be characterized as having less than 0.001% by weight of nicotine, or less than 0.0001%, or even 0% by weight of nicotine, calculated as the free base.

In some embodiments, the active ingredient comprises a nicotine component (e.g., any product or composition of the disclosure, in addition to comprising any active ingredient or combination of active ingredients as disclosed herein, may further comprise a nicotine component).

Cannabinoids

In some embodiments, the active ingredient comprises one or more cannabinoids. As used herein, the term "cannabinoid" refers to a class of diverse chemical compounds that acts on cannabinoid receptors, also known as the endocannabinoid system, in cells that alter neurotransmitter release in the brain. Ligands for these receptor proteins include the endocannabinoids produced naturally in the body by animals; phytocannabinoids, found in cannabis; and synthetic cannabinoids, manufactured artificially. Cannabinoids found in cannabis include, without limitation: cannabigerol (CBG), cannabichromene (CBC), cannabidiol (CBD), tetrahydrocannabinol (THC), cannabinol (CBN), cannabinodiol (CBDL), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethyl ether (CBGM), cannabinerolic acid, cannabidiolic acid (CBDA), cannabinol propyl variant (CBNV), cannabitriol (CBO), tetrahydrocannabinolic acid (THCA), and tetrahydrocannabivarinic acid (THCV A). In certain embodiments, the cannabinoid is selected from tetrahydrocannabinol (THC), the primary psychoactive compound in cannabis, and cannabidiol (CBD) another major constituent of the plant, but which is devoid of psychoactivity. All of the above compounds can be used in the form of an isolate from plant material or synthetically derived.

Alternatively, the active ingredient can be a cannabimimetic, which is a class of compounds derived from plants other than cannabis that have biological effects on the endocannabinoid system similar to cannabinoids. Examples include yangonin, alpha-amyrin or beta-amyrin (also classified as terpenes), cyanidin, curcumin (tumeric), catechin, quercetin, salvinorin A, N-acylethanolamines, and N-alkylamide lipids.

When present, a cannabinoid (e.g., CBD) or cannabimimetic is typically in a concentration of at least about 0.1% by weight of the composition, such as in a range from about 0.1% to about 30%, such as, e.g., from about 0.1%, about 0.2%, about 0.3%, about 0.4%, about 0.5% about 0.6%, about 0.7%, about 0.8%, or about 0.9%, to about 1%, about 2%, about 3%, about 4%, about 5%, about 6%, about 7%, about 8%, about 9%, about 10%, about 15%, about 20%, or about 30% by weight, based on the total weight of the composition.

Terpenes

Active ingredients suitable for use in the present disclosure can also be classified as terpenes, many of which are associated with biological effects, such as calming effects. Terpenes are understood to have the general formula of $(C_5H_8)_n$ and include monoterpenes, sesquiterpenes, and diterpenes. Terpenes can be acyclic, monocyclic or bicyclic in structure. Some terpenes provide an entourage effect when used in combination with cannabinoids or cannabimimetics. Examples include beta-caryophyllene, linalool, limonene, beta-citronellol, linalyl acetate, pinene (alpha or beta), geraniol, carvone, eucalyptol, menthone, iso-menthone, piperitone, myrcene, beta-bourbonene, and germacrene, which may be used singly or in combination.

Pharmaceutical Ingredients

In some embodiments, the active ingredient comprises an active pharmaceutical ingredient (API). The API can be any known agent adapted for therapeutic, prophylactic, or diagnostic use. These can include, for example, synthetic organic compounds, proteins and peptides, polysaccharides and other sugars, lipids, phospholipids, inorganic compounds (e.g., magnesium, selenium, zinc, nitrate), neurotransmitters or precursors thereof (e.g., serotonin, 5-hydroxytryptophan, oxitriptan, acetylcholine, dopamine, melatonin), and nucleic acid sequences, having therapeutic, prophylactic, or diagnostic activity. Non-limiting examples of APIs include analgesics and antipyretics (e.g., acetylsalicylic acid, acetaminophen, 3-(4-isobutylphenyl)propanoic acid), phosphatidylserine, myoinositol, docosahexaenoic-acid (DHA, Omega-3), arachidonic acid (AA, Omega-6), S-adenosylmethionine (SAM), beta-hydroxy-beta-methylbutyrate (HMB), citicoline (cytidine-5'-diphosphate-choline), and cotinine. In some embodiments, the active ingredient comprises citicoline. In some embodiments, the active ingredient is a combination of citicoline, caffeine, theanine, and ginseng. In some embodiments, the active ingredient comprises sunflower lecithin. In some embodiments, the active ingredient is a combination of sunflower lecithin, caffeine, theanine, and ginseng.

The amount of API may vary. For example, when present, an API is typically at a concentration of from about 0.001% w/w to about 10% by weight, such as, e.g., from about 0.01%, about 0.02%, about 0.03%, about 0.04%, about 0.05%, about 0.06%, about 0.07%, about 0.08%, about 0.09%, about 0.1% w/w, about 0.2%, about 0.3%, about 0.4%, about 0.5% about 0.6%, about 0.7%, about 0.8%, about 0.9%, or about 1%, to about 2%, about 3%, about 4%, about 5%, about 6%, about 7%, about 8%, about 9%, or about 10% by weight, based on the total weight of the composition.

In some embodiments, the composition is substantially free of any API. By "substantially free of any API" means that the composition does not contain, and specifically excludes, the presence of any API as defined herein, such as any Food and Drug Administration (FDA) approved therapeutic agent intended to treat any medical condition.

Sweeteners

The composition typically further comprises one or more sweeteners. The sweeteners can be any sweetener or combination of sweeteners, in natural or artificial form, or as a combination of natural and artificial sweeteners. Examples of natural sweeteners include isomaltulose, fructose, sucrose, glucose, maltose, mannose, galactose, lactose, stevia, honey, and the like. Examples of artificial sweeteners include sucralose, maltodextrin, saccharin, aspartame, acesulfame K, neotame and the like. In some embodiments, the sweetener comprises one or more sugar alcohols. Sugar alcohols are polyols derived from monosaccharides or disaccharides that have a partially or fully hydrogenated form. Sugar alcohols have, for example, about 4 to about 20 carbon atoms and include erythritol, arabitol, ribitol, isomalt, maltitol, dulcitol, iditol, mannitol, xylitol, lactitol, sorbitol, and combinations thereof (e.g., hydrogenated starch hydrolysates). When present, a representative amount of sweetener may make up from about 0.1 to about 30 percent or more of the of the composition by weight, for example, from about 5 to about 28%, from about 10 to about 26%, from about 15 to about 25%, or from about 20 to about 25% of the composition on a weight basis, based on the total dry weight of the composition. In certain embodiments, the sweetener (or combination of sweeteners) is present in an amount of about 5 to about 30% by weight (e.g., about 8 to about 25%).

In some embodiments, the products of the disclosure can be characterized as completely free or substantially free of sugar alcohols generally or isomalt specifically. For example, certain embodiments can be characterized as having less than 1% by dry weight, or less than 0.5% by weight, or less than 0.1% by weight of sugar alcohols generally or isomalt specifically, or 0% by weight of sugar alcohols generally or isomalt specifically.

Salts

In some embodiments, the composition may further comprise a salt (e.g., alkali metal salts), typically employed in an amount sufficient to provide desired sensory attributes to the composition. Non-limiting examples of suitable salts include sodium chloride, potassium chloride, ammonium chloride, flour salt, and the like. The salts may also include alkali metal buffers such as metal carbonates (e.g., potassium carbonate or sodium carbonate), or metal bicarbonates such as sodium bicarbonate, and the like.

When present, a representative amount of salt is about 0.1 percent by dry weight or more, about 1.0 percent by weight or more, or at about 1.5 percent by weight or more, but will typically make up about 10 percent or less of the total dry weight of the composition, or about 7.5 percent or less or about 5 percent or less (e.g., about 0.5 to about 5 percent by weight). In certain embodiments, the composition includes about 0.1 to about 5% by dry weight of one or more alkali metal salts (e.g., about 0.1 to about 2% or about 0.5 to about 1.5%).

Natural Gum

In certain embodiments, the composition includes a gum, for example, a natural gum. As used herein, a natural gum refers to polysaccharide materials of natural origin that have binding properties, and which are also useful as a thickening or gelling agents. Representative natural gums derived from plants, which are typically water soluble to some degree, include xanthan gum, guar gum, gum arabic, ghatti gum, gum tragacanth, karaya gum, locust bean gum, gellan gum, and combinations thereof. When present, natural gum binder materials are typically present in an amount of up to about 5% by dry weight, for example, from about 0.1, about 0.2, about 0.3, about 0.4, about 0.5, about 0.6, about 0.7, about 0.8, about 0.9, or about 1%, to about 2, about 3, about 4, or about 5% by weight.

Humectants

In certain embodiments, one or more humectants may be employed in the composition. Examples of humectants include, but are not limited to, glycerin, propylene glycol, and the like. Humectants can impact mouthfeel and other organoleptic properties of the composition, and will also impact water activity of the composition.

When present, a humectant will typically make up about 25% or less of the dry weight of the composition (e.g., from about 0.5 to about 20% by weight). When present, a representative amount of humectant is about 0.1% to about 20% by weight, or about 10% to about 15% by weight.

Binding Agents

An additional binder component may be employed in certain embodiments, in amounts sufficient to provide the desired physical attributes and organoleptic properties to the composition. Binding agents typically also function as viscosity modifiers, thickening agents, or gelling agents. Typical binders can be organic or inorganic, or a combination thereof. Representative binders include modified cellulose, povidone, sodium alginate, starch-based binders, pectin, carrageenan, pullulan, zein, and the like, and combinations thereof. In some embodiments, the binder comprises pectin or carrageenan or combinations thereof.

The amount of binder utilized in the composition can vary, but is typically up to about 30 dry weight percent, and certain embodiments are characterized by a binder content of at least about 0.1% by weight, such as about 1 to about 30% by weight, or about 5 to about 10% by weight, based on the total dry weight of the composition.

Organic Acid

As used herein, the term "organic acid" refers to an organic (i.e., carbon-based) compound that is characterized by acidic properties. Typically, organic acids are relatively weak acids (i.e., they do not dissociate completely in the presence of water), such as carboxylic acids ($—CO_2H$) or sulfonic acids ($—SO_2OH$). As used herein, reference to organic acid means an organic acid that is intentionally added. In this regard, an organic acid may be intentionally added as a specific composition ingredient as opposed to merely being inherently present as a component of another composition ingredient (e.g., the small amount of organic acid which may inherently be present in a composition ingredient such as a tobacco material).

In some embodiments, the one or more organic acids are added neat (i.e., in their free acid, native solid or liquid form) or as a solution in, e.g., water. In some embodiments, the one or more organic acids are added in the form of a salt, as described herein below.

In some embodiments, the organic acid is an alkyl carboxylic acid. Non-limiting examples of alkyl carboxylic acids include formic acid, acetic acid, propionic acid, octanoic acid, nonanoic acid, decanoic acid, undecanoic acid, dodecanoic acid, stearic acid, oleic acid, linoleic acid, linolenic acid, and the like. In some embodiments, the organic acid is an alkyl sulfonic acid. Non-limiting examples of alkyl sulfonic acids include propanesulfonic acid and octanesulfonic acid.

In some embodiments, the organic acid is citric acid, malic acid, tartaric acid, octanoic acid, benzoic acid, a toluic acid, salicylic acid, or a combination thereof. In some embodiments, the organic acid is benzoic acid. In some embodiments, the organic acid is citric acid.

In alternative embodiments, a portion, or even all, of the organic acid may be added in the form of a salt with an alkaline component, which may include, but is not limited to, nicotine. Non-limiting examples of suitable salts, e.g., for nicotine, include formate, acetate, propionate, isobutyrate, butyrate, alpha-methylbutyate, isovalerate, beta-methylvalerate, caproate, 2-furoate, phenylacetate, heptanoate, octanoate, nonanoate, oxalate, malonate, glycolate, benzoate, tartrate, levulinate, ascorbate, fumarate, citrate, malate, lactate, aspartate, salicylate, tosylate, succinate, pyruvate, and the like. In some embodiments, the organic acid or a portion thereof may be added in the form of a salt with an alkali metal such as sodium, potassium, and the like. In organic acids having more than one acidic group (such as a di-or-tri-carboxylic acid), in some instances, one or more of these acid groups may be in the form of such a salt. Suitable non-limiting examples include monosodium citrate, disodium citrate, and the like. In some embodiments, the organic acid is a salt of citric acid, malic acid, tartaric acid, octanoic acid, benzoic acid, a toluic acid, salicylic acid, or a combination thereof. In some embodiments, the organic acid is a mono or di-ester of a di- or tri-carboxylic acid, respectively, such as a monomethyl ester of citric acid, malic acid, or tartaric acid, or a dimethyl ester of citric acid.

The amount of organic acid present in the composition may vary. Generally, the composition comprises from about 0.1 to about 10% by dry weight of organic acid, present as one or more organic acids, based on the total weight of the composition. In some embodiments, the composition comprises about 0.1%, about 0.2%, about 0.3%, about 0.4%, about 0.5%, about 0.6%, about 0.7%, about 0.8%, about 0.9%, about 1%, about 2%, about 3%, about 4%, about 5%, about 6%, about 7%, about 8%, about 9%, or about 10% organic acid by weight, based on the total weight of the composition. In some embodiments, the composition comprises from about 0.1 to about 0.5% by weight of organic acid, for example, about 0.1, about 0.15, about 0.2, about 0.25, about 0.3, about 0.35, about 0.4, about 0.45, or about 0.5% by weight, based on the total weight of the composition. In some embodiments, the composition comprises from about 0.25 to about 0.35% by weight of organic acid, for example, from about 0.25, about 0.26, about 0.27, about 0.28, about 0.29, or about 0.3, to about 0.31, about 0.32, about 0.33, about 0.34, or about 0.35% by weight. In the case where a salt of an organic acid is added, the percent by weight is calculated based on the weight of the free acid, not including any counter-ion which may be present.

The quantity of acid present will vary based on the acidity and basicity of other components which may be present in the composition (e.g., nicotine, salts, buffers, and the like). Accordingly, in certain embodiment, the organic acid is provided in a quantity sufficient to provide a pH of 7.0 or below, (typically about 6.8 or below, about 6.6 or below, or about 6.5 or below) of the composition. In certain embodiments the acid inclusion is sufficient to provide a composition pH of from about 4.0 to about 7.0; for example, from about 4.5, about 5.0, about 5.5, or about 6.0, to about 6.5, or about 7.0. In some embodiments, the organic acid is provided in a quantity sufficient to provide a pH of the composition of from about 5.5 to about 6.5, for example, from about 5.5, about 5.6, about 5.7, about 5.8, about 5.9, or about 6.0, to about 6.1, about 6.2, about 6.3, about 6.4, or about 6.5.

Buffering Agents

In certain embodiments, the composition of the present disclosure can comprise additional pH adjusters or buffering agents. Examples of pH adjusters and buffering agents that can be used include, but are not limited to, metal hydroxides (e.g., alkali metal hydroxides such as sodium hydroxide and potassium hydroxide), and other alkali metal buffers such as metal carbonates (e.g., potassium carbonate or sodium carbonate), or metal bicarbonates such as sodium bicarbonate, and the like. The amounts of buffering agent utilized can vary, depending in part on the presence (and amount) of pH-modifying components in the composition, such as organic acids, nicotine salts, and the like. Where present, the buffering agent is typically present in an amount less than about 5 percent based on the dry weight of the composition, for example, from about 0.5% to about 5%, such as, e.g., from about 0.75% to about 4%, from about 0.75% to about 3%, or about 0.5% to about 1.5%, or from about 1% to about 2% by weight. Non-limiting examples of suitable buffers include alkali metals acetates, glycinates, phosphates, glycerophosphates, citrates, carbonates, hydrogen carbonates, borates, certain amino acids (e.g., glycine or glycylglycine), or mixtures thereof.

Colorants

A colorant may be employed in amounts sufficient to provide the desired physical attributes to the composition. Examples of colorants include various dyes and pigments, such as caramel coloring and titanium dioxide. The amount of colorant utilized in the composition can vary, but when present is typically up to about 3 dry weight percent, such as from about 0.1%, about 0.5%, or about 1%, to about 3% by weight.

Tobacco Material

In some embodiments, the composition may include a tobacco material. The tobacco material can vary in species, type, and form. Generally, the tobacco material is obtained from for a harvested plant of the *Nicotiana* species. Example *Nicotiana* species include N. tabacum, N. rustica, N. alata, N. arentsii, N. excelsior, N. forgetiana, N. glauca, N. glutinosa, N. gossei, N. kawakamii, N. knightiana, N. langsdorffi, N. otophora, N. setchelli, N. sylvestris, N. tomentosa, N. tomentosiformis, N. undulata, N. x sanderae, N. africana, N. amplexicaulis, N. benavidesii, N. bonariensis, N. debneyi, N. longiflora, N. maritina, N. megalosiphon, N. occidentalis, N. paniculata, N. plumbaginifolia, N. raimondii, N. rosulata, N. simulans, N. stocktonii, N. suaveolens, N. umbratica, N. velutina, N. wigandioides, N. acaulis, N. acuminata, N. attenuata, N. benthamiana, N. cavicola, N. clevelandii, N. cordifolia, N. corymbosa, N. fragrans, N. goodspeedii, N. linearis, N. miersii, N. nudicaulis, N. obtusifolia, N. occidentalis subsp. Hersperis, N. pauciflora, N. petunioides, N. quadrivalvis, N. repanda, N. rotundifolia, N. solanifolia, and N. spegazzinii. Various representative other types of plants from the *Nicotiana* species are set forth in Goodspeed, *The Genus Nicotiana*, (Chonica Botanica) (1954); U.S. Pat. No. 4,660,577 to Sensabaugh, Jr. et al.; U.S. Pat. No. 5,387,416 to White et al., U.S. Pat. No. 7,025,066 to Lawson et al.; U.S. Pat. No. 7,798,153 to Lawrence, Jr. and U.S. Pat. No. 8,186,360 to Marshall et al.; each of which is incorporated herein by reference. Descriptions of various types of tobaccos, growing practices and harvesting practices are set forth in *Tobacco Production, Chemistry and Technology*, Davis et al. (Eds.) (1999), which is incorporated herein by reference.

*Nicotiana* species from which suitable tobacco materials can be obtained can be derived using genetic-modification or crossbreeding techniques (e.g., tobacco plants can be genetically engineered or crossbred to increase or decrease production of components, characteristics or attributes). See, for example, the types of genetic modifications of plants set forth in U.S. Pat. No. 5,539,093 to Fitzmaurice et al.; U.S. Pat. No. 5,668,295 to Wahab et al.; U.S. Pat. No. 5,705,624 to Fitzmaurice et al.; U.S. Pat. No. 5,844,119 to Weigl; U.S. Pat. No. 6,730,832 to Dominguez et al.; U.S. Pat. No. 7,173,170 to Liu et al.; U.S. Pat. No. 7,208,659 to Colliver et al. and U.S. Pat. No. 7,230,160 to Benning et al.; U.S. patent application Pub. No. 2006/0236434 to Conkling et al.; and PCT WO2008/103935 to Nielsen et al. See, also, the types of tobaccos that are set forth in U.S. Pat. No. 4,660,577 to Sensabaugh, Jr. et al.; U.S. Pat. No. 5,387,416 to White et al.; and U.S. Pat. No. 6,730,832 to Dominguez et al., each of which is incorporated herein by reference.

Various parts or portions of the plant of the *Nicotiana* species can be included within a composition as disclosed herein. For example, virtually all of the plant (e.g., the whole plant) can be harvested, and employed as such. Alternatively, various parts or pieces of the plant can be harvested or separated for further use after harvest. For example, the flower, leaves, stem, stalk, roots, seeds, and various combinations thereof, can be isolated for further use or treatment. In some embodiments, the tobacco material comprises tobacco leaf (lamina). The composition disclosed herein can include processed tobacco parts or pieces, cured and aged tobacco in essentially natural lamina and/or stem form, a tobacco extract, extracted tobacco pulp (e.g., using water as a solvent), or a mixture of the foregoing (e.g., a mixture that combines extracted tobacco pulp with granulated cured and aged natural tobacco lamina).

In certain embodiments, the tobacco material is used in a form that can be described as particulate (i.e., shredded, ground, granulated, or powder form). The manner by which the tobacco material is provided in a finely divided or powder type of form may vary. Preferably, plant parts or pieces are comminuted, ground or pulverized into a particulate form using equipment and techniques for grinding, milling, or the like.

For the preparation of oral products, it is typical for a harvested plant of the *Nicotiana* species to be subjected to a curing process. The tobacco materials incorporated within the composition for inclusion within products as disclosed herein are those that have been appropriately cured and/or aged. Descriptions of various types of curing processes for various types of tobaccos are set forth in *Tobacco Production, Chemistry and Technology*, Davis et al. (Eds.) (1999). Examples of techniques and conditions for curing flue-cured tobacco are set forth in Nestor et al., *Beitrage Tabakforsch. Int.,* 20, 467-475 (2003) and U.S. Pat. No. 6,895,974 to Peele, which are incorporated herein by reference. Representative techniques and conditions for air curing tobacco are set forth in U.S. Pat. No. 7,650,892 to Groves et al.; Roton et al., *Beitrage Tabakforsch. Int.,* 21, 305-320 (2005) and Staaf et al., *Beitrage Tabakforsch. Int.,* 21, 321-330 (2005), which are incorporated herein by reference. Certain types of tobaccos can be subjected to alternative types of curing processes, such as fire curing or sun curing.

In certain embodiments, tobacco materials that can be employed include flue-cured or Virginia (e.g., K326), burley, sun-cured (e.g., Indian Kurnool and Oriental tobaccos, including Katerini, Prelip, Komotini, Xanthi and Yambol tobaccos), Maryland, dark, dark-fired, dark air cured (e.g., Madole, Passanda, Cubano, Jatin and Bezuki tobaccos), light air cured (e.g., North Wisconsin and Galpao tobaccos), Indian air cured, Red Russian and Rustica tobaccos, as well as various other rare or specialty tobaccos and various blends of any of the foregoing tobaccos.

Tobacco materials used in the present disclosure can be subjected to, for example, fermentation, bleaching, and the like. If desired, the tobacco materials can be, for example, irradiated, pasteurized, or otherwise subjected to controlled heat treatment. Such treatment processes are detailed, for example, in U.S. Pat. No. 8,061,362 to Mua et al., which is incorporated herein by reference. In certain embodiments, tobacco materials can be treated with water and an additive capable of inhibiting reaction of asparagine to form acrylamide upon heating of the tobacco material (e.g., an additive selected from the group consisting of lysine, glycine, histidine, alanine, methionine, cysteine, glutamic acid, aspartic acid, proline, phenylalanine, valine, arginine, compositions incorporating di- and trivalent cations, asparaginase, certain non-reducing saccharides, certain reducing agents, phenolic compounds, certain compounds having at least one free thiol group or functionality, oxidizing agents, oxidation catalysts, natural plant extracts (e.g., rosemary extract), and combinations thereof. See, for example, the types of treatment processes described in U.S. Pat. Nos. 8,434,496, 8,944,072, and 8,991,403 to Chen et al., which are all incorporated herein by reference. In certain embodiments, this type of treatment is useful where the original tobacco material is subjected to heat in the processes previously described.

Tobacco materials can be whitened in certain embodiments according to any means known in the art. For example, bleached tobacco material produced by various whitening methods using various bleaching or oxidizing agents and oxidation catalysts can be used. Example oxidizing agents include peroxides (e.g., hydrogen peroxide), chlorite salts, chlorate salts, perchlorate salts, hypochlorite salts, ozone, ammonia, potassium permanganate, and combinations thereof. Example oxidation catalysts are titanium dioxide, manganese dioxide, and combinations thereof. Processes for treating tobacco with bleaching agents are discussed, for example, in U.S. Pat. No. 787,611 to Daniels, Jr.; U.S. Pat. No. 1,086,306 to Oelenheinz; U.S. Pat. No. 1,437,095 to Delling; U.S. Pat. No. 1,757,477 to Rosenhoch; U.S. Pat. No. 2,122,421 to Hawkinson; U.S. Pat. Nos. 2,148,147; 2,170,107; and 2,274,649 to Baier; U.S. Pat. No. 2,770,239 to Prats et al.; U.S. Pat. Nos. 3,612,065; 3,851,653; and 3,889,689 to Rosen; U.S. Pat. No. 3,943,940 to Minami; U.S. Pat. No. 3,943,945 to Rosen; U.S. Pat. No. 4,143,666 to Rainer; U.S. Pat. No. 4,194,514 to Campbell; U.S. Pat. Nos. 4,366,823, 4,366,824, and 4,388,933 to Rainer et al.; U.S. Pat. No. 4,641,667 to Schmekel et al.; U.S. Pat. No. 5,713,376 to Berger; U.S. Pat. No. 9,339,058 to Byrd Jr. et al.; U.S. Pat. No. 9,420,825 to Beeson et al.; and U.S. Pat. No. 9,950,858 to Byrd Jr. et al.; as well as in US Pat. App. Pub. No. 2012/0067361 to Bjorkholm et al.; US Pat. App. Pub. No. 2016/0073686 to Crooks; UA Pat. App. Pub. No. 2017/0020183 to Bjorkholm; and US Pat. App. Pub. No. 2017/0112183 to Bjorkholm, and in PCT Publ. Appl. Nos. WO1996/031255 to Giolvas and WO2018/083114 to Bjorkholm, all of which are incorporated herein by reference.

In some embodiments, the whitened tobacco material can have an ISO brightness of at least about 50%, at least about 60%, at least about 65%, at least about 70%, at least about 75%, or at least about 80%. In some embodiments, the whitened tobacco material can have an ISO brightness in the range of about 50% to about 90%, about 55% to about 75%, or about 60% to about 70%. ISO brightness can be measured according to ISO 3688:1999 or ISO 2470-1:2016.

In some embodiments, the whitened tobacco material can be characterized as lightened in color (e.g., "whitened") in comparison to an untreated tobacco material. White colors are often defined with reference to the International Commission on Illumination's (CIE's) chromaticity diagram. The whitened tobacco material can, in certain embodiments, be characterized as closer on the chromaticity diagram to pure white than an untreated tobacco material.

In various embodiments, the tobacco material can be treated to extract a soluble component of the tobacco material therefrom. "Tobacco extract" as used herein refers to the isolated components of a tobacco material that are extracted from solid tobacco pulp by a solvent (e.g., an aqueous solvent) that is brought into contact with the tobacco material in an extraction process. Various extraction techniques of tobacco materials can be used to provide a tobacco extract and tobacco solid material. See, for example, the extraction processes described in US Pat. Appl. Pub. No. 2011/0247640 to Beeson et al., which is incorporated herein by reference. Other example techniques for extracting components of tobacco are described in U.S. Pat. No. 4,144,895 to Fiore; U.S. Pat. No. 4,150,677 to Osborne, Jr. et al.; U.S. Pat. No. 4,267,847 to Reid; U.S. Pat. No. 4,289,147 to Wildman et al.; U.S. Pat. Nos. 4,351,346; and 4,359,059 to Brummer et al.; U.S. Pat. No. 4,506,682 to Muller; U.S. Pat. No. 4,589,428 to Keritsis; U.S. Pat. No. 4,605,016 to Soga et al.; U.S. Pat. No. 4,716,911 to Poulose et al.; U.S. Pat. No. 4,727,889 to Niven, Jr. et al.; U.S. Pat. No. 4,887,618 to Bernasek et al.; U.S. Pat. No. 4,941,484 to Clapp et al.; U.S. Pat. No. 4,967,771 to Fagg et al.; U.S. Pat. No. 4,986,286 to Roberts et al.; U.S. Pat. No. 5,005,593 to Fagg et al.; U.S. Pat. No. 5,018,540 to Grubbs et al.; U.S. Pat. No. 5,060,669 to White et al.; U.S. Pat. No. 5,065,775 to Fagg; U.S. Pat. Nos. 5,074,319; 5,099,862; and 5,121,757 to White et al.; U.S. Pat. No. 5,131,414 to Fagg; U.S. Pat. No. 5,131,415 to Munoz et al.; U.S. Pat. No. 5,148,819 to Fagg; U.S. Pat. No. 5,197,494 to Kramer; U.S. Pat. No. 5,230,354 to Smith et al.; U.S. Pat. No. 5,234,008 to Fagg; U.S. Pat. No. 5,243,999 to Smith; U.S. Pat. No. 5,301,694 to Raymond et al.; U.S. Pat. No. 5,318,050 to Gonzalez-Parra et al.; U.S. Pat. No. 5,343,879 to Teague; U.S. Pat. No. 5,360,022 to Newton; U.S. Pat. No. 5,435,325 to Clapp et al.; U.S. Pat. No. 5,445,169 to Brinkley et al.; U.S. Pat. No. 6,131,584 to Lauterbach; U.S. Pat. No. 6,298,859 to Kierulff et al.; U.S. Pat. No. 6,772,767 to Mua et al.; and U.S. Pat. No. 7,337,782 to Thompson, all of which are incorporated by reference herein. Tobacco extracts can be utilized in a spray-dried or freeze-dried form.

Typical inclusion ranges for tobacco materials can vary depending on the nature and type of the tobacco material, and the intended effect on the final composition, with an example range of up to about 60% by dry weight (or up to about 50% by weight or up to about 40% by weight or up to about 30% by weight). In some embodiments, the products of the disclosure can be characterized as completely free or substantially free of tobacco material (other than purified nicotine as an active ingredient). For example, certain embodiments can be characterized as having less than 1% by dry weight, or less than 0.5% by weight, or less than 0.1% by weight of tobacco material, or 0% by weight of tobacco material.

Other Additives

Other additives can be included in the disclosed composition. For example, the composition can be processed, blended, formulated, combined and/or mixed with other materials or ingredients. The additives can be artificial, or can be obtained or derived from herbal or biological sources. Examples of further types of additives include thickening or gelling agents (e.g., fish gelatin), emulsifiers, oral care additives (e.g., thyme oil, eucalyptus oil, and zinc), preservatives (e.g., potassium sorbate and the like), zinc or magnesium salts selected to be relatively water soluble for compositions with greater water solubility (e.g., magnesium or zinc gluconate) or selected to be relatively water insoluble for compositions with reduced water solubility (e.g., magnesium or zinc oxide), or combinations thereof.

See, for example, those representative components, combination of components, relative amounts of those components, and manners and methods for employing those components, set forth in U.S. Pat. No. 9,237,769 to Mua et al., U.S. Pat. No. 7,861,728 to Holton, Jr. et al., U.S. Pat. App. Pub. No. 2010/0291245 to Gao et al., and U.S. Pat. App. Pub. No. 2007/0062549 to Holton, Jr. et al., each of which is incorporated herein by reference. Typical inclusion ranges for such additional additives can vary depending on the nature and function of the additive and the intended effect on the final composition, with an example range of up to about 10% by weight, based on total weight of the composition (e.g., about 0.1 to about 5% by weight or about 0.5% to about 1.5%).

The aforementioned additives can be employed together (e.g., as additive formulations) or separately (e.g., individual additive components can be added at different stages involved in the preparation of the final composition). Furthermore, the aforementioned types of additives may be encapsulated as provided in the final product or composition. Exemplary encapsulated additives are described, for example, in WO2010/132444 to Atchley, which has been previously incorporated by reference herein.

In some embodiments, one or more components of the composition (e.g., a filler or a tobacco material) can be described as a particulate material. As used herein, the term "particulate" refers to a material in the form of a plurality of individual particles, some of which can be in the form of an agglomerate of multiple particles, wherein the particles have an average length to width ratio less than 2:1, such as less than 1.5:1, such as about 1:1. In various embodiments, the particles of a particulate material can be described as substantially spherical or granular.

The particle size of a particulate material may be measured by sieve analysis. As the skilled person will readily appreciate, sieve analysis (otherwise known as a gradation test) is a method used to measure the particle size distribution of a particulate material. Typically, sieve analysis involves a nested column of sieves which comprise screens, preferably in the form of wire mesh cloths. A pre-weighed sample may be introduced into the top or uppermost sieve in the column, which has the largest screen openings or mesh size (i.e. the largest pore diameter of the sieve). Each lower sieve in the column has progressively smaller screen openings or mesh sizes than the sieve above. Typically, at the base of the column of sieves is a receiver portion to collect any particles having a particle size smaller than the screen opening size or mesh size of the bottom or lowermost sieve in the column (which has the smallest screen opening or mesh size).

In some embodiments, any particulate material referenced herein (e.g., filler component or tobacco material) can be characterized as having at least 50% by weight of particles with a particle size as measured by sieve analysis of no greater than about 1000 µm, such as no greater than about 500 µm, such as no greater than about 400 µm, such as no greater than about 350 µm, such as no greater than about 300 µm. In some embodiments, at least 60% by weight of the particles of any particulate material referenced herein have a particle size as measured by sieve analysis of no greater than about 1000 µm, such as no greater than about 500 µm, such as no greater than about 400 µm, such as no greater than about 350 µm, such as no greater than about 300 µm. In some embodiments, at least 70% by weight of the particles of any particulate material referenced herein have a particle size as measured by sieve analysis of no greater than about 1000 µm, such as no greater than about 500 µm, such as no greater than about 400 µm, such as no greater than about 350 µm, such as no greater than about 300 µm. In some embodiments, at least 80% by weight of the particles of any particulate material referenced herein have a particle size as measured by sieve analysis of no greater than about 1000 µm, such as no greater than about 500 µm, such as no greater than about 400 µm, such as no greater than about 350 µm, such as no greater than about 300 µm. In some embodiments, at least 90% by weight of the particles of any particulate material referenced herein have a particle size as measured by sieve analysis of no greater than about 1000 µm, such as no greater than about 500 µm, such as no greater than about 400 µm, such as no greater than about 350 µm, such as no greater than about 300 µm. In some embodiments, at least 95% by weight of the particles of any particulate material referenced herein have a particle size as measured by sieve analysis of no greater than about 1000 µm, such as no greater than about 500 µm, such as no greater than about 400 µm, such as no greater than about 350 µm, such as no greater than about 300 µm. In some embodiments, at least 99% by weight of the particles of any particulate material referenced herein have a particle size as measured by sieve analysis of no greater than about 1000 µm, such as no greater than about 500 µm, such as no greater than about 400 µm, such as no greater than about 350 µm, such as no greater than about 300 µm. In some embodiments, approximately 100% by weight of the particles of any particulate material referenced herein have a particle size as measured by sieve analysis of no greater than about 1000 µm, such as no greater than about 500 µm, such as no greater than about 400 µm, such as no greater than about 350 µm, such as no greater than about 300 µm. In certain embodiments, at least a portion of the particles have a particle size as measured by sieve analysis of about 100 µm or less, about 50 µm or less, or about 30 µm or less.

Preparation of the Composition

The compositions of the invention are prepared, for example, by dry-blending dry ingredients, such as filler, sweeteners, salts, and the like. In certain embodiments, water can be added to the dry blend at this stage. Additionally, it is optional to add, such as by spraying, active ingredients and/or flavoring agents to the dry blend, followed by mixing.

The lipid is typically heated to slightly above the melting temperature such that the lipid is liquefied. Optionally, active ingredients, flavoring agents, and/or lecithin can be added to the liquefied lipid at this stage.

Thereafter, all or a portion of the liquefied lipid can be blended with the dry blend and mixed until the composition reaches the desired level of homogeneity or until the desired textural properties are achieved. Thee composition can be divided into discrete portions, such as by pouring the composition into a sheet-like structure, cooling, and then cutting the structure into individual portions, or by depositing the composition into molds and allowing to cool.

The various components of the composition may be contacted, combined, or mixed together using any mixing technique or equipment known in the art. Any mixing method that brings the mixture ingredients into intimate contact can be used, such as a mixing apparatus featuring an impeller or other structure capable of agitation. Examples of mixing equipment include roll mills, casing drums, conditioning cylinders or drums, liquid spray apparatus, conical-type blenders, ribbon blenders, mixers available as FKM130, FKM600, FKM1200, FKM2000 and FKM3000 from Littleford Day, Inc., Plough Share types of mixer cylinders, Hobart mixers, and the like. See, for example, the types of methodologies set forth in U.S. Pat. No. 4,148,325 to Solomon et al.; U.S. Pat. No. 6,510,855 to Korte et al.; and U.S. Pat. No. 6,834,654 to Williams, U.S. Pat. No. 4,725,440 to Ridgway et al., and U.S. Pat. No. 6,077,524 to Bolder et al., each of which is incorporated herein by reference.

Configured for Oral Use

Provided herein is a product configured for oral use. The term "configured for oral use" as used herein means that the product is provided in a form such that during use, one or more of the components of the composition (e.g., flavoring agents and/or nicotine) passes into the mouth of the user. In certain embodiments, the product is adapted to deliver components to a user through mucous membranes in the user's mouth and, in some instances, said component is an active ingredient (including, but not limited to, for example, nicotine) that can be absorbed through the mucous membranes in the mouth when the product is used.

The composition of the disclosure is typically used in discrete portions that can be individually placed in the mouth of the user. If desired, the composition could be placed in a pouch, as for example, as a particulate or granular material.

In certain embodiments, the amount of the composition of the disclosure administered per discrete portion is between about 25 mg to about 1500 mg, such as about 50 mg to about 1200 mg. Where the composition of the invention includes an active ingredient, such as nicotine, in certain embodiments, the amount of active ingredient administered per discrete portion or unit is between about 0.1 mg to about 10 mg, such as about 0.2 to about 7.5 mg, or about 1 to about 5 mg.

Many modifications and other embodiments of the invention will come to mind to one skilled in the art to which this invention pertains having the benefit of the teachings presented in the foregoing description. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

EXPERIMENTAL

Aspects of the present invention are more fully illustrated by the following examples, which are set forth to illustrate certain aspects of the present invention and are not to be construed as limiting thereof.

Example 1

A composition with low water content (less than 5% by total weight) comprising the ingredients set forth in Table 1 below is prepared.

TABLE 1

| Ingredient | Amount (g) | Amount (% by dry weight) |
| --- | --- | --- |
| Palm oil | 4500 | 45 |
| Microcrystalline cellulose (MCC) | 5130 | 51.3 |
| Nicotine | 210 | 2.1 |
| Sodium chloride | 100 | 1.0 |
| Lecithin | 40 | 0.4 |
| Sucralose | 15 | 0.15 |
| Flavoring agent | 5 | 0.05 |

The composition is prepared as follows:

1. Weigh out MCC, salt, sucralose, and flavoring agent and blend in a metal bowl.
2. Weigh out palm oil in another bowl and melt to a liquid state by heating to 40-45° C. Add nicotine and lecithin to liquefied composition.
3. Weigh about a third of the blend from Step 2 and place in a separate bowl.
4. Add the dry-blended material from Step 1 to the melted blend from Step 3. This should form loose clumps that form into a ball when squeezed by hand.
5. Run material from Step 4 through a roll mill (4 passes) to blend components.
6. Using a heated metal bowl (40-45° C.), continue mixing the refined material from Step 5 while slowly adding the remaining melted mixture from Step 2. Continue this step until the composition is a flowable slurry.
7. Deposit into mold and allow to cool and harden. Target weight is 1.3 g/piece.

Example 2

The same composition of Example 1 is made using the same general method, except the nicotine is sprayed as a solution onto the dry-blended components rather than added to the molten lipid.

Example 3

Example 1 is repeated, except 3% HPC by dry weight is added to dry blend of Step 1, reducing the MCC amount by 3%.

Example 4

Example 1 is repeated, except additional water is added to the dry blend of Step 1 such that the total water content of the final composition is about 15% by weight.

Example 5

Example 1 is repeated, except additional water is added to the dry blend of Step 1 such that the total water content of the final composition is about 25% by weight.

Example 6

Example 4 is repeated, except MCC is replaced with one or more sugar alcohols.

Example 7

Example 5 is repeated, except MCC is replaced with one or more sugar alcohols.

Example 8

Example 1 is repeated, except palm oil is replaced with a blend of palm oil and palm kernel oil.

Example 9

Example 1 is repeated, except palm oil is replaced with a blend of palm kernel oil and soybean oil.

Example 10

Example 1 is repeated, except palm oil is replaced with cottonseed oil.

Example 11

Example 1 is repeated, except palm oil is replaced with a blend of palm kernel oil, soybean oil, and cottonseed oil.

What is claimed is:

1. A composition comprising: microcrystalline cellulose in an amount from about 40% to about 70% by weight, based on the weight of the composition, a lipid having a melting point of about 29° C. or above, the lipid present in an amount from about 30% to about 60% by weight, based on the weight of the composition, water in an amount by weight of less than 7.5%, based on the weight of the composition, nicotine in an amount from about 0.5% to about 5% by weight, based on the weight of the composition, lecithin in an amount from about 0.1% to about 5% by weight, based on the weight of the composition, and sodium chloride in an amount from about 0.1% to about 5% by weight, based on the weight of the composition, wherein the composition is substantially free of isomalt and substantially free of tobacco material, excluding any nicotine component present.

2. The composition of claim 1, wherein the lipid has a melting point of about 36° C. to about 45° C.

3. The composition of claim 1, wherein the lipid is selected from the group consisting of palm oil, palm kernel oil, soybean oil, cottonseed oil, and combinations thereof.

4. The composition of claim 1, wherein the filler further comprises a cellulose derivative.

5. The composition of claim 4, wherein the cellulose derivative is hydroxypropylcellulose.

6. The composition of claim 1, comprising less than about 5% water by weight, based on the total weight of the composition.

* * * * *